Figure 1:
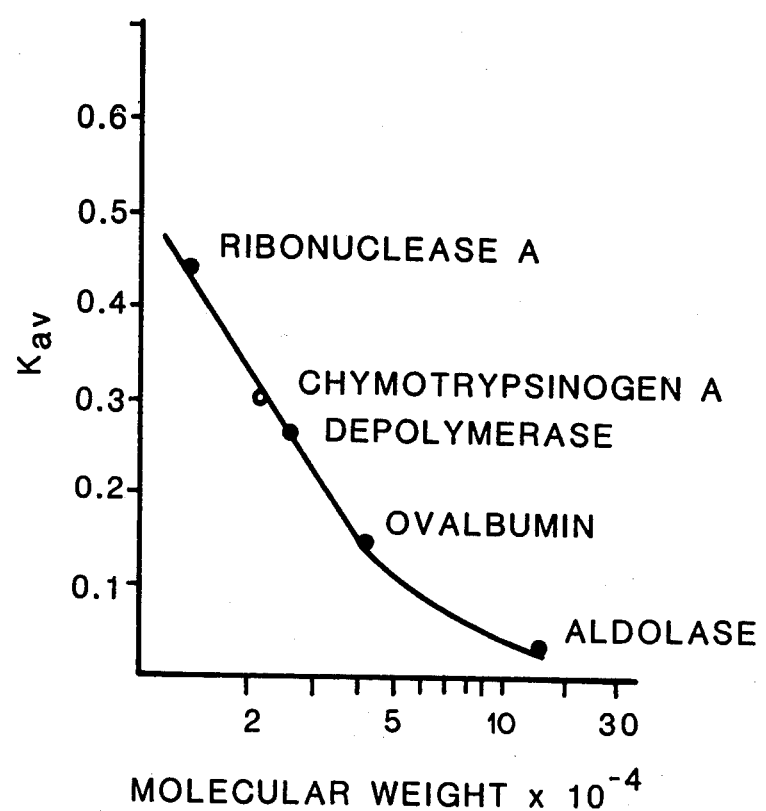

United States Patent [19]

Vandenbergh et al.

[11] Patent Number: 4,783,406

[45] Date of Patent: Nov. 8, 1988

[54] METHOD AND COMPOSITIONS FOR USE IN THE TREATMENT OF FIREBLIGHT

[75] Inventors: Peter A. Vandenbergh, Sarasota, Fla.; Anne K. Vidaver, Lincoln, Nebr.

[73] Assignee: Microlife Technics, Inc., Sarasota, Fla.

[21] Appl. No.: 920,754

[22] Filed: Oct. 20, 1986

Related U.S. Application Data

[62] Division of Ser. No. 662,065, Oct. 18, 1984, Pat. No. 4,678,750.

[51] Int. Cl.$^4$ .................. C12N 9/24; A61K 37/48
[52] U.S. Cl. .................... 435/200; 435/847; 424/94.61
[58] Field of Search .................. 435/200, 847

[56] References Cited

PUBLICATIONS

Hartung, J. S. et al., Phytopathology 72, 945 (1982).
Vidaver, A. K., et al., J. Virol. 4:300–308 (1969).
Yamamoto et al., Virol. 40: 734–744 (1970).
Vidaver, A. K., J. Appl. Microbiol. 15: 1523–1524 (1967).
Fairbridge, R. A., et al., Biochem, J. 49: 423–427 (1951).
Koch A. et al., Anal. Biochem, 44: 239–245 (1971).
Liu, P. V., et al., J. Infect. Dis. 108: 218–228 (1961).
Weber, K., et al., J. Biol. Chem. 244: 4406–4412 (1969).
Brewer, J. M. et al., Experimental Techniques in Biochemistry, Electrophoreses, pp. 128–160 (1974).
Merrill, et al., Science 211: 1437–1438 (1981).

*Primary Examiner*—Thomas G. Wiseman
*Assistant Examiner*—Charles L. Patterson, Jr.
*Attorney, Agent, or Firm*—Ian C. McLeod

[57] ABSTRACT

A method and compositions for the treatment of fireblight disease in plants are described. The compositions include a phage for *Erwinia amylovora* which produces fireblight and an enzyme produced by the phage which depolymerizes a polysaccharide produced by *Erwinia amylovora* which is the cause of the fireblight disease. Purified enzyme preparations are described.

5 Claims, 1 Drawing Sheet

METHOD AND COMPOSITIONS FOR USE IN THE TREATMENT OF FIREBLIGHT

This application is a division of application Ser. No. 662,065, filed Oct. 18, 1984, now U.S. Pat. No. 4,678,750.

BACKGROUND OF THE INVENTION (1) Field of the Invention

The present invention relates to a method and compositions for the treatment of fireblight in plants which is caused by *Erwinia amylovora*. In particular the present invention relates to the use of mixtures of a phage for the *Erwinia amylovora* and an enzyme produced by a phage for the *Erwinia amylovora* in the treatment of this plant disease.

(2) Prior Art

Fireblight disease in plants is caused by an extracellular polysaccharide produced by *Erwinia amylovora*. It is a large molecular weight polymeric anion which interferes with the transport of nutrients in the infected plant. The result is that the plant leaves and buds die from lack of nutrients.

Various methods have been suggested by the prior art for the treatment of fireblight. Included is the use of various antibiotics which kill the *Erwinia amylovora*. The problem with this method is that mutant strains are produced over time which are resistant to the antibiotic. Other methods suggested include applying other strains or species of bacteria usually of the genus Erwinia to the plant in order to displace the *Erwinia amylovora* by population dominance. The problem with this method is that it involves the release of large numbers of bacteria into the environment and it is not particularly successful.

Polysaccharide depolymerases have been described for bacteriophage infected bacteria, particularly *Erwinia amylovora* by Hartung, J. S. et al in Phytopathology 72 945(1982). Phage infection results in the induction of enzymes that degrade the capsular polysaccharide of the host. No use was described for the depolymerase enzyme which was in impure form.

OBJECTS

It is therefore an object of the present invention to provide a novel method for the destruction of *Erwinia amylovora* on the plants as well as the polysaccharide. Further it is an object of the present invention to provide a method which is relatively economical and effective. These and other objects will become increasingly apparent by reference to the following description and the drawing.

IN THE DRAWING

FIG. 1 is a graph showing the basis for estimation of the molecular weight of the depolymerase enzyme from *Erwinia amylovora* described herein.

GENERAL DESCRIPTION

The present invention relates to a composition for the treatment of fireblight in plants which is caused by an *Erwinia amylovora* having as the characteristic of producing a capsular polysaccharide responsible for the fireblight in the plants which comprises in admixture: a phage which lyses the *Erwinia amylovora*; and a polysaccharide depolymerase enzyme produced by a phage which lyses the *Erwinia amylovora*, wherein the composition contains at least about $10^6$ pfu of the phage per gram of the composition. Further the present invention relates to the method of treatment of fireblight in affected plants caused by an *Erwinia amylovora* having as the characteristic of producing a capsular polysaccharide responsible for the fireblight in the plants which comprises applying to the plants an effective amount of a phage which lyses an *Erwinia amylovora*; and a depolymerase enzyme for depolymerizing the polysaccharide produced by a phage which lyses the *Erwinia amylovora*.

The preferred Erwinia phage depolymerase enzyme described herein was purified from crude bacterial lysates produced by the propagation of a specific bacteriophage ERA103 (ATCC 39824 B1) in cultures of *Erwinia amylovora*. Conventional methods using ammonium sulfate precipitation of the enzyme, ultracentrifugation and gel filtration chromatography were used for enzyme purification. The isolation of a bacteriophage from infected plant tissue, the purification and partial characterization of the polysaccharide depolymerase from phage-infected *Erwinia amylovora* NCPPB595 (ATCC 39824), and its application for the biological control of fireblight using Bartlett pear seedling is described.

SPECIFIC DESCRIPTION

Bacteriophage Isolation.

Twigs of fireblight infected tissue from apples and pears were obtained from Michigan, Montana, Colorado, Illinois and Washington. Enrichment for bacteriophages were essentially as described by Vidaver, A. K. et al in *J. Virol.* 4:300–308 (1969). Two to five grams of infected twigs were washed with tap water, homogenized in 100 to 200 ml of sterile phosphate buffer (0.0125 M, pH 7.1) with a Waring blender, and the suspensions centrifuged at low speed. The supernatant was collected and 10 ml was added to 10 ml of *Erwinia amylovora* NCPPB595 at about $3 \times 10^8$ CFU/ml in NBY broth. After overnight incubation at 25° C. on a rotary shaker (250 rpm), the cultures were centrifuged at low speed to pellet the bacteria. The supernatant was decanted into sterile tubes, chloroform (10% v/v) was added and after vortex mixing, the chloroform was allowed to settle out. Aliquots were diluted in NBY broth, and 10 ul were plated in duplicate with 0.1 ml of the respective mid-exponential phase enriching host, and independently, with the other *Erwinia amylovora* strains, in a soft agar overlay (Vidaver, A. K. et al., J. Virol. 4:300–308 (1969). Plates were examined for phages after incubation overnight at 25° C.

Many phages were isolated from the different *Erwinia amylovora* strains. Of the four samples that yielded phages producing plaques with turbid halos, host range studies showed no differences among them. Differences in the size of turbid halos was taken as an indicator of differences in potential quantity of depolymerase activity of the enzyme produced by the phage. Therefore, the phage ERA103, with the largest halo, was chosen as typical. It produced a clear plaque of one-to-three mm, surrounded by a turbid halo of five-to-seven mm. *E. herbicola* M232A (ATCC 31225) was insensitive to all the phages.

Bacteriophage Characterization and Purification

Phage ERA103 was purified by three successive plaque pickings, and after uniformity of plaque morphology was ascertained, small volume (10 ml) lysates were prepared by adding phage at a ratio of 1 PFU/$10^4$ CFU/ml of exponential phase cells ($1 \times 2 \times 10^8$ CFU/ml). Incubation was for four to six hours at 25° C. on a shaker (200 rpm). After increase, high titer lysates were obtained by adding phages at a ratio of 1:10 phage:CFU. After incubation for three to four hours at 25° C., the preparations were chloroform treated as above and stored at 4° C.

The preparation then was concentrated by the polyethylene glycol (PEG) procedure of Yamamoto et al., (Yamamoto, K. R., et al., Virol. 40:734–744 (1970)). Debris was sedimented at low speed (2,000 x g) for 10 min, followed by the addition of 10% PEG to the supernatant, and NaCl to a final concentration of 0.5 M. The mixture was chilled one hour, and the phage pelleted at 10,000 x g for 20 min. The pellet was resuspended and stored in chilled 0.0125 M phosphate buffer, pH 7.1.

The partial purification of ERA103 by plaque picking, lysate production and PEG precipitation yielded 10 ml of high-titer ($10^{11}$–$10^{12}$) PFU/ml lysates from 100 ml cultures. Pellets from the PEG treatment contained more than 99% of the total PFU. Lysates did not clear during phage release, but turbidity decreases were always detected which indicated lysis of cells of *E. amylovora* ATCC 39824.

EXAMPLE I

Production of Enzyme in Phage-Infected Cultures and Purification

Depolymerase activity in phage-infected bacteria was produced in the following manner. *Erwinia amylovora* NCPPB595 (ATCC 39824) cells were grown for 18 hours in 200 ml of N broth (Vidaver, A. K., J. Appl. Microbiol. 15:1523–1524 (1967)), supplemented with 0.25% yeast extract at 25° C. on a New Brunswick aerating shaker at 250 rpm. This culture was used to inoculate 2000 ml of N broth supplemented with 0.25% yeast extract at 25° C. and shaken at 250 rpm. Early log phase cells, $4.0\times10^8$ CFU/ml, of this culture were infected with phage at a multiplicity of infection of 2. Incubation was continued for 10 hours. The lysates were then stored at 4° C. for 11 hours and then purified as follows:

Step 1. Crude lysate. The active lysate from 21 of phage-infected cells was centrifuged in a Sorvall RC-3 centrifuge at 8,000 x g for 30 minutes to pellet the bacterial cells.

Step 2. Ammonium sulfate precipitation. Solid ammonium sulfate was added slowly with stirring to the supernatant fluid to give a final concentration of 45% saturation; this solution was allowed to remain at 4° C. overnight. This solution was then centrifuged at 18,000 x g for 30 minutes. The pellet was collected and resuspended in 30 ml of 0.01M citrate buffer pH 6, containing 0.01 M 2-mercaptoethanol. The dissolved precipitate was then subjected to dialysis against 3 liters of 0.01 M citrate buffer, pH 6.0 containing 0.01 M 2-mercaptoethanol for 18 hours.

Step 3. Ultracentrifugation. The resuspended ammonium sulfate precipitate was centrifuged in a Sorvall OTD-65B ultracentrifuge at 82,000 x g for 2 hours. The supernatant was collected and frozen at −20° C.

Step 4. CM-Sephadex TM batchwise separation. The supernatant from the previous step was then subjected to further purification using CM-Sephadex TM C-50 (supplied by Sigma) in a batch procedure. The CM-Sephadex was swollen in 0.01 M citrate buffer, pH 6.0 containing 0.01 M 2-mercaptoethanol. The enzyme preparation, 20 ml, was added to 200 ml of the ion exchange material and slowly stirred for 1 hour. The slurry was then filtered through a Buchner funnel, washed with 200 ml of citrate buffer, collected, dialyzed against citrate buffer containing 2-mercaptoethanol, and concentrated using Carbowax 20, (Fisher Co.).

Step 5. Passage through a Sephadex TM G-50 column. The concentrated enzyme preparation was then subjected to ascending gel filtration on a 2.6 cm×65 column of Sephadex G-50 equilibrated in 0.01 M citrate buffer, pH 6.0 containing 0.01 M 2-mercaptoethanol. The column was equilibrated and washed with buffer. The fractions were assayed and those with enzymatic activity were then dialyzed and concentrated.

Step 6 Passage through a Sephacryl TM S-200 column. The concentrated enzyme fractions were subjected to ascending gel filtration on a 2.6 cm×75 cm column of Sephacryl TM S-200 (supplied by Sigma) equilibrated in 0.01 M citrate buffer, pH 6.0 containing 0.01 M 2-mercaptoethanol. The column was washed with buffer and the enzymatic fractions were dialyzed and concentrated.

The enzyme was precipitated at 45% $(NH_4)_2SO_4$ saturation. Ethanol precipitation was also attempted but resulted in a diminished yield. The ultracentrifugation procedure demonstrated that the activity was present in the supernatant and that no activity was associated with the pellet. The recovered enzyme was treated with CM-Sephadex TM C-50 in a batchwise procedure followed by gel filtration using Sephadex TM G-50 and Sephacryl TM S-200 (Table 1).

TABLE 1

Purification of depolymerase from phage-infected *E. amylovora* NCPPB595

| Procedure | Vol (ml) | Enzyme[a] units | Protein (mg/ml) | Enzyme[b] sp.act. | % Recovery | Purification[c] |
|---|---|---|---|---|---|---|
| 45% $(NH_4)_2SO_4$ precipitate | 30 | 528 | 2.4 | 220 | 100 | — |
| 82,000 × g supernatant | 30 | 361 | 1.4 | 258 | 68 | 1.2 |
| CM-Sephadex C-50 batchwise | 15 | 250 | 0.6 | 417 | 23 | 1.9 |
| Sephadex G-50 column | 12 | 277 | 0.12 | 2309 | 21 | 10.4 |
| Sephacryl S-200 column | 3 | 333 | 0.10 | 3330 | 6 | 15.0 |

[a] One unit is the amount of enzyme required to produce 1 micromole of galactose equivalent per minute under standard assay conditions.

[b] Units per milligram of protein.

[c] Because of interfering substances, depolymerase was not assayed in crude lysates; any purification achieved by the initial ammonium sulfate fractionation is therefore not included.

Several 280 nm absorbing protein peaks were observed in the Sephadex TM G-50 elution profile, depolymerase activity was associated with only one of them. Two protein peaks were observed in the elution profile of the Sephacryl TM S-200 column. Substitution of ion exchange chromatography with either Sephadex TM DEAE A-25 or Sephadex TM QAE A-50 (supplied by Sigma), instead of gel filtration did not improve the purification of the enzyme. Each step of the purification was monitored using polyacrylamide gel electrophoresis of concentrated enzyme preparations.

Characterization of Enzyme. Estimation of Enzymatic Activity.

Depolymerase activity was assayed by following the release of galactose from the polysaccharide substrate according to the method of Fairbridge (Fairbridge, R. A., et al. Biochem. J. 49:423-427 (1951)). The reaction mixture consisted of the following: 100 microliters of the appropriate enzyme solution and 100 microliters of polysaccharide (10 mg/ml) suspended in 0.01 M citrate buffer, pH 6.0 containing 0.01 M 2-mercaptoethanol. One unit of enzyme was defined as the amount of enzyme required to produce 1 micromole of galactose per minute under standard assay conditions.

Protein Assay.

Protein concentrations were determined using the microbiuret method of Koch (Koch, A. et al., Anal. Biochem. 44:239-245 (1971)).

Substrate Preparation.

Polysaccharide was prepared from uninfected cultures of Erwinia amylovora NCPPB595 cultivated on sheets of cellophane overlaying Tryptic Soy agar, as decribed by Liu (Liu, P. V., et al., J. Infect. Dis. 108:218-228 (1961)). The polysaccharide was extracted from the slime layer according to the method of Liu.

Molecular Weight Determination.

The molecular weight of the depolymerase was determined by ascending gel filtration on a 2.6 cm×75 cm column of Sephacryl TM S-200 equilibrated in 0.01M citrate buffer, pH 6.0 containing 0.01 M 2-mercaptoethanol. A Pharmacia calibration kit containing various molecular weight protein markers was used as standards. Sodium dodecyl sulfate (SDS)-polyacrylamide gel electrophoresis was also used for determination of the molecular weight (Weber, K., et al., J. Biol. Chem. 244:4406–4412 (1969)).

Slab Polyacrylamide Gel Electrophoresis.

Electrophoresis of the enzymatic preparations was performed utilizing the method of Brewer (Brewer, J. M., et al., Electrophoresis, pp 128-160 (1974)). The gels were silver stained according to the method of Merril (Merril, C. R., et al., Science 211:1437-1438 (1981)).

The activity of purified depolymerase was tested under different conditions. Activity appeared stable after storage at −20° C. for several weeks. After assaying depolymerase activity at several pH values from 3.0–8.0 in different buffers, optimal activity was achieved at pH 6.0. Temperature studies employing a 10 minute preincubation of the enzyme at various temperatures from 15°–45° C., showed that 30° C. was optimum for activity.

EXAMPLE II

The effect of various chemical agents on depolymerase activity can be seen in Table 2.

TABLE 2

| Agent | Concentration[a] | Activity[b] % Control |
|---|---|---|
| p-Chloromercuribenzoate | 10.0 | 0 |
|  | 1.0 | 0 |
|  | 0.1 | 0 |
| Iodoacetate | 10.0 | 100 |
|  | 1.0 | 100 |
|  | 0.1 | 100 |
| N—ethylmaleimide | 10.0 | 100 |
|  | 1.0 | 100 |

TABLE 2-continued

| Agent | Concentration[a] | Activity[b] % Control |
|---|---|---|
|  | 0.1 | 100 |
| Sodium azide | 10.0 | 100 |
|  | 1.0 | 100 |
|  | 0.1 | 100 |
| Potassium cyanide | 10.0 | 100 |
|  | 1.0 | 100 |
|  | 0.1 | 100 |
| 2-Mercaptoethanol | 10.0 | 168 |
|  | 1.0 | 155 |
|  | 0.1 | 122 |
| Dithiothreitol | 10.0 | 258 |
|  | 1.0 | 138 |
|  | 0.1 | 122 |
| Ethylenediaminetetraacetate | 10.0 | 100 |
|  | 1.0 | 100 |
|  | 0.1 | 100 |
| Ethylene-di-(o-hydroxyphenyl-acetate | 10.0 | 100 |
|  | 1.0 | 100 |
|  | 0.1 | 100 |

[a] Concentration is in millimoles per liter
[b] % Activity is based on a control assay without inhibitors The enzyme was insensitive to a variety of agents such as, sodium azide, potassium cyanide, ethylenediaminetetraacetate, ethylene-di-(o-hydroxyphenylacetate) and 8-hydroxyquinoline. The thiol group alkylators such as N-ethylmaleimide and iodoacetate had no effect on enzymatic activity, however, p-chloromercuribenzoate inhibited the enzyme at all concentrations tested. The reducing agents 2-mercaptoethanol and dithiothreitol (1,4 dimercapto-2,3-butanediol) both enhanced depolymerase activity substantially for reasons not completely understood.

The molecular weight of depolymerase was estimated by ascending gel filtration chromatography with Sephacryl TM S-200. By comparing the elution volume of the enzymatic activity with the elution volumes of standard proteins, (ribonuclease a, chymotrypsinogen a, ovalbumin and aldolase) a molecular weight of about 21,000 was estimated (FIG. 1).

EXAMPLE III Efficaciousness of Enzyme

The enzymatic fraction 82,000 x g supernatant with phage ERA103 was testing for ability to control Erwinia amylovora infections in Bartlett pear seedlings.

Bartlett pear seedlings 3 weeks old, at the four leaf pair stage were utilized. The plants were wounded 1 cm below the apex using a 26 gauge needle, piercing the stem completely. The plants were then atomized with 0.5 ml of the enzyme preparation where appropriate, and allowed to air dry 15 minutes. The plants were then spray challenged with different concentrations of Erwinia amylovora followed by another application of the enzyme and phage, where appropriate. In infected plants it would be rare to have more than the number of bacteria per plant that are provided by $10^6$ CFU per ml. The results are shown in Table 3.

TABLE 3

| Buffer control[a] | 0/3[c,d] |
|---|---|
| 10% Enzyme control[b] | 0/3 |
| Disease control | 3/3 |
| 2 × $10^8$ CFU Erwinia amylovora per ml of spray solution |  |
| Disease control | 5/5 |
| 2 × $10^6$ CFR Erwinia amylovora per ml of spray solution |  |
| 10% by volume Enzyme and | 5/5 |
| 2 × $10^8$ CFU Erwinia amylovora per ml of spray solution |  |

TABLE 3-continued

| | |
|---|---|
| 10% by weight Enzyme and 2 × $10^6$ CFR *Erwinia amylovora* per ml of spray solution | 0/5 |
| 1% Enzyme and 2 × $10^6$ CFR *Erwinia amylovora* per ml of spray solution | 4/5 |

[a]Buffer is 0.01 M sodium citrate pH 6.0 containing 0.01 M 2-mercaptoethanol.
[b]Enzymatic fraction contains 1 × $10^7$ PFU per ml of phage.
[c]Numerator represents the number of diseased plants, denominator represents the total number of the plants.
[d]Results compiled after 10 days.

The results indicated that the enzyme preparation containing phage gave complete control of disease when applied at rate of 10%. When enzyme containing $1\times10^7$ PFU phage per ml was applied at a usage rate of 1% enzyme only 20% protection was observed.

As can be seen from the foregoing description and Example III the enzyme and phage combination provides very effective control of fireblight in plants. The enzyme and phage can be applied separately if this is desirable for any reason.

We claim:

1. A purified enzyme preparation which comprises a depolymerase for a polysaccharide produced by *Erwinia amylovora,* the depolymerase being derived from a phage which lyses the *Erwinia amylovora,* and having a molecular weight of about 21,000 and an optimal depolymerase activity at pH 6 and independently an optimal depolymerase activity at 30° C.

2. The purified enzyme preparation of claim 1 wherein the enzyme has been derived from culturing phage ERA 103 deposited as ATCC 39824 Bl with subsequent enzyme purification of the enzyme.

3. The enzyme preparation of claim 1 in admixture with a stabilizing agent.

4. The enzyme preparation of claim 3 wherein the stabilizing agent is selected from mercaptoethanol or dithiothreitol at a concentration between about 0.1 mM and 10 mM.

5. The enzyme preparation of claim 1 wherein the enzyme has a specific activity of about 200 to 3500 units per milligram of a proteinaceous material containing the enzyme.

* * * * *